United States Patent [19]

Busco

[11] 4,000,749
[45] Jan. 4, 1977

[54] ISOLATION MODULE
[75] Inventor: Francis J. Busco, Big Sur, Calif.
[73] Assignee: Float, Big Sur, Calif.
[22] Filed: May 30, 1975
[21] Appl. No.: 582,448
[52] U.S. Cl. .................................. 135/1 R; 4/171;
    4/172.11; 52/2; 128/1 B; 135/1 C; 135/3 E
[51] Int. Cl.² .................................... A45F 1/02
[58] Field of Search ....... 128/1 R, 1 B, 149, 145 R,
    128/191 A, 376; 135/1 R, 1 C, 3 B, 4 C; 52/2;
    9/1 A, 2 A, 3, 11 A; 4/171, 172, 172.12

[56] References Cited
UNITED STATES PATENTS

| | | | |
|---|---|---|---|
| 2,723,660 | 11/1955 | Greenberg | 128/1 R |
| 2,804,633 | 9/1957 | Taylor et al. | 52/2 |
| 2,908,919 | 10/1959 | Bicknell et al. | 52/2 |
| 3,034,154 | 5/1962 | Silverstone | 9/11 A |
| 3,345,996 | 10/1967 | Sadove et al. | 135/1 R |
| 3,540,170 | 11/1970 | Flowers | 135/1 R |
| 3,729,002 | 4/1973 | Miller | 128/1 B |
| 3,809,065 | 5/1974 | Gatts | 128/1 B |
| 3,818,896 | 6/1974 | Deaton | 128/1 B |
| 3,883,913 | 5/1975 | Givens | 9/1 A |

FOREIGN PATENTS OR APPLICATIONS 164,040  2/1949  Austria ............... 128/1 R Primary Examiner—Werner H. Schroeder
Assistant Examiner—Conrad L. Berman
Attorney, Agent, or Firm—Oblon, Fisher, Spivak, McClelland & Maier

[57] ABSTRACT

A structure is disclosed which is particularly suitable for isolating individuals from all types of environmental stimuli. The structure is portable and includes a inflatable housing having a liquid containing portion at the base thereof. A high density liquid, such as a salt saturated water solution, is placed in the water containing compartment to provide a floatation pool which can accommodate human beings. A temperature control system is provided for maintaining the interior at a constant temperature, and a system is also provided for supplying fresh breathing air and for purifying the fluid.

16 Claims, 5 Drawing Figures

ISOLATION MODULE

BACKGROUND OF THE INVENTION

1. Field of the Invention:

The present invention relates to an apparatus for providing an isolated environment, and more particularly to a portable apparatus having an inflatable wall structure for providing an isolated environment for one or more individuals.

2. Description of the Prior Art:

Isolation tanks were first developed in 1954 by John C. Lilly to study what the human brain would do when cut off from all external sensory input. The purpose of isolation tanks is to prevent, as much as possible, any external stimuli from reaching an individual within the isolation tank, since it has been found that such isolation provides great psychological and physical benefits. An analysis of the benefits provided by the use of isolation tanks may be found in John C. Lilly's book, *The Center Of the Cyclone*, The Julian Press, New York (1972), as well as other works by the same author.

Isolation tanks developed in the past are generally constructed of heavy rigid and dense materials such as concrete, wood and other conventional building materials. Such tanks and their enclosures are accordingly very expensive and time consuming to construct. Furthermore, they are not portable and must therefore be constructed on permanently dedicated land.

These characteristics of presently known isolation tanks have greatly limited their use and sale due to the fact that only a limited number of people could afford such devices and owned sufficient areas of land to permit their construction.

Furthermore, in some instances it was found that the massive and rigid materials of such previously known tanks failed to provide adequate isolation from certain types of environmental stimuli, particularly low frequency accoustic energy of the type generated by earth tremors, heavy traffic and the like. Accordingly a need exists for isolation tanks permitting greater isolation from low frequency accoustical stimuli.

Thus a need exists for a low cost, easily assembled, portable isolation tank structure that provides greater isolation than known devices, particularly in terms of attenuating low frequency accoustic stimuli. In this regard it is further pointed out that low frequency stimuli are often the most discomforting since in many cases they cannot be specifically identified by those experiencing them, with the result that they become subconsciously discomforting. Thus complete relaxation cannot adequately be achieved unless low frequency stimuli are eliminated.

SUMMARY OF THE INVENTION

Accordingly, one object of the present invention is the provision of a novel isolation tank structure.

Yet another object of the present invention is the provision of an inflatable structure suitable for use as an isolation tank and an enclosure therefor.

A still further object of the present invention is the provision of a low cost, portable isolation tank and enclosure which may be constructed from low cost materials and assembled in a very short time.

Yet another object of the present invention is the provision of a low cost, inflatable isolation tank structure which is easily transportable.

Yet another object of the present invention is provision of a novel isolation tank structure which is particularly suitable for preventing the penetration of low frequency accoustic stimuli.

Yet another object of the present invention is the provision of an isolation tank structure including an inflatable pool enclosure and environmental housing in which an individual can be completely surrounded by a controlled environment bounded by soft and resilient boundary surfaces.

Briefly, these and other objects of the present invention are achieved by the provision of an inflatable structure which includes a pool enclosure including an inflatable rim for containing a high density fluid and having a floor formed of a series of inflatable members for completely supporting the high density fluid on a cushion of air or another suitable gas. A tent-like enclosure including inflatable walls is attached to the pool structure to form a complete enclosure of a sufficient size to be inhabited by one or more individuals. Temperature control and filtration systems are provided for maintaining the high density fluid at a predetermined temperature level and in a highly purified state.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
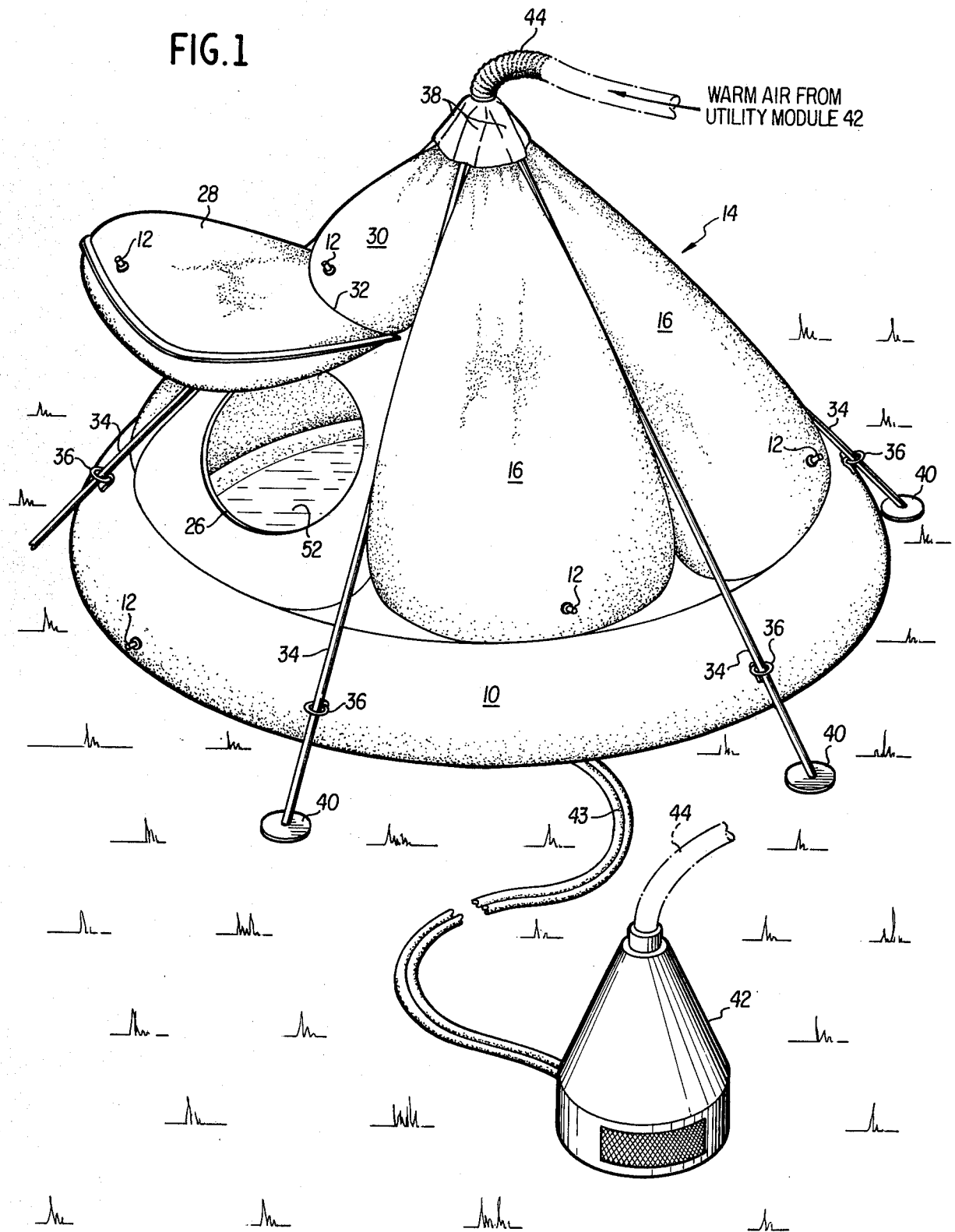
FIG. 1 is an illustration of the apparatus of the present invention fully inflated and in operating condition.

Referring now to the drawings, wherein like reference numerals designate identical or corresponding parts throughout the several views, and more particularly to FIG. 1 thereof, the general configuration of a first embodiment of the present invention is illustrated. More particularly, the illustrated structure is shown as including an inflatable base tube 10 which surrounds the entire lower periphery of the illustrated structure and acts as a pool wall structure for containing a pool of a dense fluid. The base tube 10 is preferably constructed of a conventional plastic material, such as polyethylene, having a reasonably light weight but being tough and highly puncture resistant. The base tube is inflatable by means of a suitable valve 12 through which air, or another suitable gas such as carbon dioxide may be blown or pumped. Inflation can be carried out in any conventional manner through the use of a conventional air pump or by coupling a pressurized gas cylinder to the valve 12. The device can be inflated directly by an individual simply by blowing into the valve 12, although the large volume of air required makes this technique of inflation somewhat impractical and suitable only for situations in which no other convenient means of inflation is available. The pressure required to adequately inflate the base tube is relatively low, in the range between 0.1 and 1 pound per square inch, although pressures above and below these values can naturally be used as circumstances require.

An environmental housing 14 is attached to an upper portion of the base tube 10 for enclosing the region surrounded by the base tube. The environmental housing 14 is preferably comprised of a plurality of interconnected individually inflatable panels 16. Each of the panels 16 is preferably constructed of two sheets of polyethylene plastic, or a suitable equivalent material, preferably the same as that of the base tube 10. The two sheets of material are bonded or thermally welded together around the peripheral portions thereof to form an air tight chamber which can be inflated to a suitable pressure, preferably in the range mentioned above, whereby each of the panel 16 becomes somewhat rigid and takes on structural strength. Each of the panels 16 is equipped with a valve 12 for inflation in the same manner as described previously with regard to the base tube 10.

Figure 2:
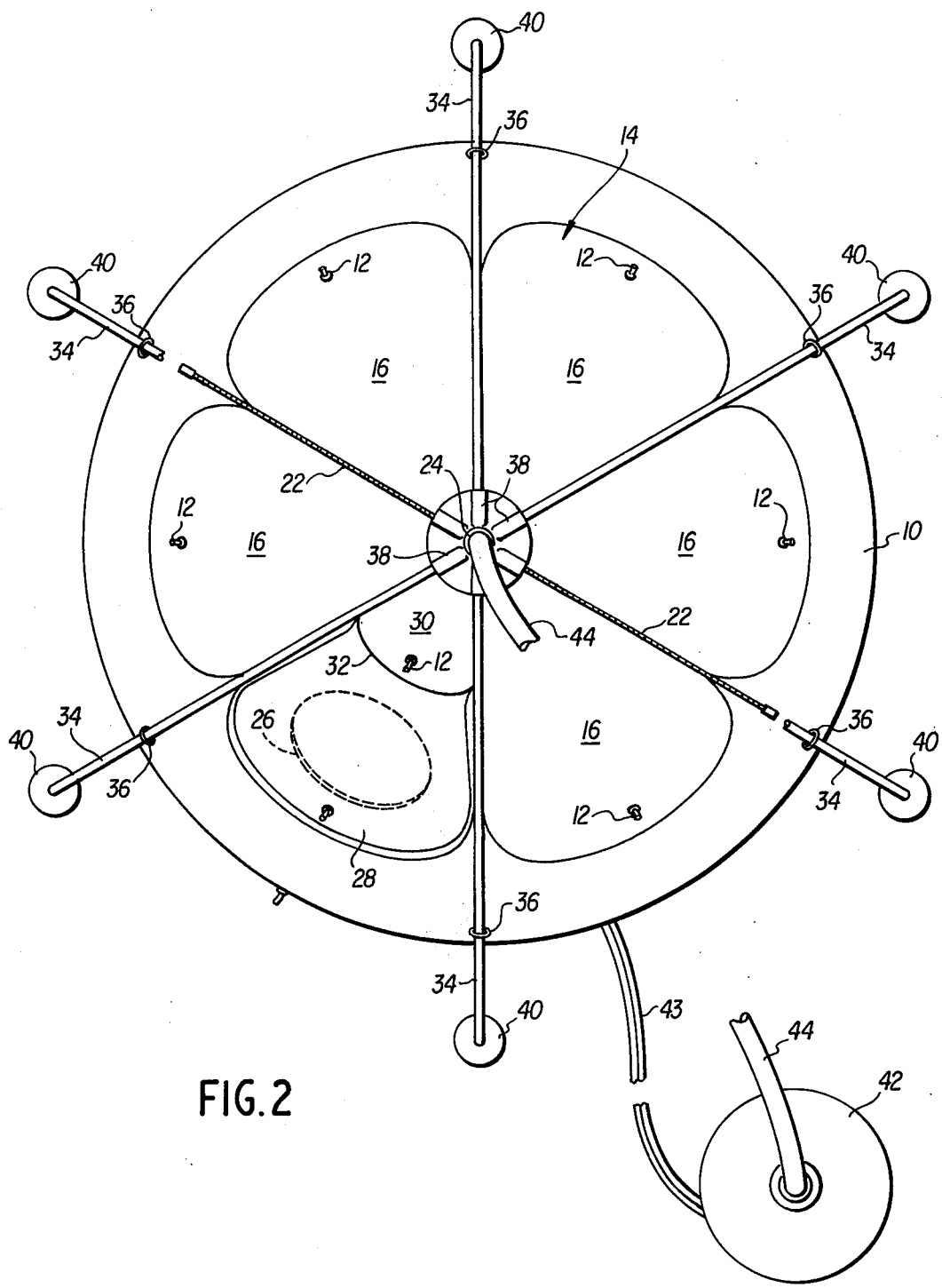
FIG. 2 is a top view of the apparatus illustrated in FIG. 1.

Referring now to FIG. 2, the structure of the environmental housing 14 is shown from the top in its inflated state. As shown, each of the panels 16 has a generally triangular shape reaching a peak 18 at a point which is at essentially the top of the isolation module when inflated, and has a rounded bottom portion 20 positioned adjacent to the base tube 10. The panels 16 may be divided into two groups of three detachably coupled together by means of a pair of zippers 22 in order to facilitate folding and packing of the isolation module.

Each group of three panels 16 may be formed of two large polyethylene sheets cut to the appropriate shape and divided into air-tight compartments by conventional plastic welding or bonding techniques to form the individual panels 16. Alternatively, each panel may be assembled from separate polyethylene sheets which are subsequently bonded together to form the complete structure. The two groups of panels are then bonded or otherwise secured to the base tube 10 according to conventional techniques to form a structurally reliable although not necessarily air tight joint. An opening 24 is left at the peak of the environmental housing 14 to permit a suitable airhose to be coupled to the environmental housing.

Although six panels are shown comprising the sides of the environmental housing 14, it will be appreciated by those skilled in the art that more or fewer panels can be used depending upon the size and configuration of the desired environmental housing. One of the panels 16 is modified to include an opening 26 for permitting individuals to enter and leave the interior of the environmental housing. An inflatable door panel 28 is secured to the modified panel having the opening 26 for the purpose of closing the opening to fully seal the interior of the environmental housing. This inflatable door panel, which is shown in the open position in FIG. 1 and in the closed position in FIG. 2, includes an upper inflatable portion 30 in addition to the inflatable door panel 28. The two portions of the door panel are separated by a weld seam 32 so that the inflatable portion 30 and the door panel may be separately inflated.

Although the various panels 16 and the door panel structure have been disclosed as being isolated from one another so that each may be inflated individually, the present invention may also be modified to include air channels coupling two or more of the inflatable panels so that the joined panels may be inflated simultaneously. This modification of the invention permits greater ease in inflating the structure and reduces the number of valves required.

Referring again to FIG. 1, a plurality of support poles 34 are shown connected to the isolation module by means of coupling rings 26 located near the juncture between the base tube 10 and the environmental housing 14 and coupled to the top portion of the environmental housing by insertion into a plurality of pockets 38 formed in a reinforced plastic ring secured around the peak of the environmental housing 14. Each of the support poles 34 may also include a foot portion 40 having a ground penetrating spike (not shown) on the lower surface thereof for securing the lower portion of each support pole to the ground and for preventing slippage thereof. The support poles are secured to the environmental housing to provide an external skeleton for stabilizing the housing and for maintaining it in proper position both while it is being inflated and during normal usage. The structure of the support poles, their coupling to the environmental housing and the manner in which the plastic materials forming the housing are secured together are all individually conventional aspects of the present invention, well known to those skilled in the art. Thus, different types of support poles, fastening members and plastic welding and bonding techniques and materials may be used within the scope of the present invention.

A utility module 42 is shown coupled through an airhose 44 to the peak of the environmental housing 14 and through a pair of fluid hoses 46 to the interior of the base tube 10. The utility module 42 contains all of the air and fluid handling equipment required to continuously supply fresh air and tempered water to the interior of the apparatus of the present invention. The utility module is preferably an electric powered apparatus, although other conventional power sources may also be used, and is provided with hoses of sufficient length so that it may be positioned at a distance from the environmental housing so that the sounds of its motor, pumps, etc. cannot be heard within the environmental housing.

Figure 3:
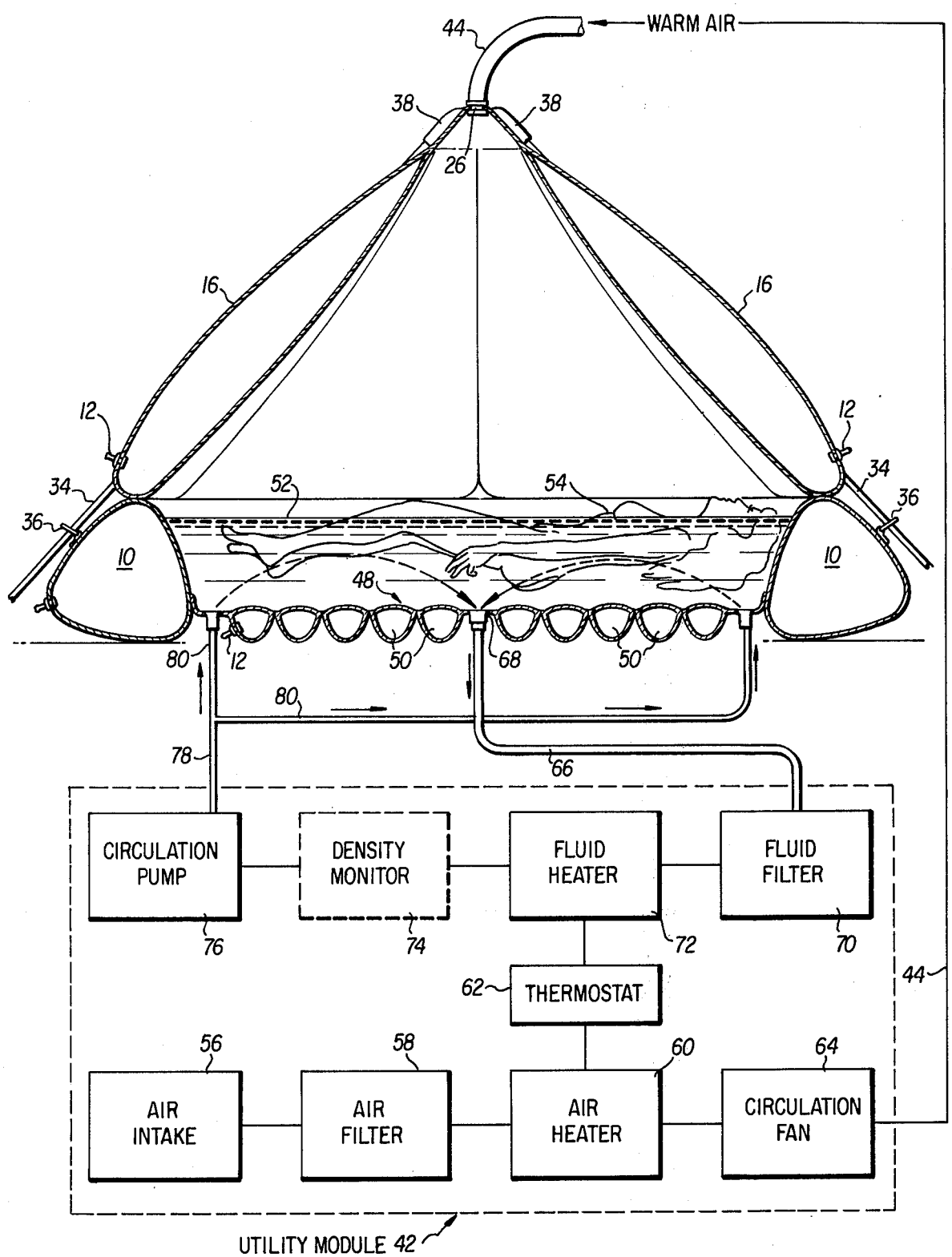
FIG. 3 is a cut-away side view of the apparatus illustrated in FIG. 1 showing the interior thereof and also including a block diagram of the air and fluid circulating system of the present invention.

Attention is now directed to FIG. 3 illustrating the interior of the environmental module of the present invention and also illustrating in the form of a block diagram the air and fluid handling components contained in the utility module 42. As shown in FIG. 3, a floor structure 48 is bonded to the inner periphery of the base tube 10 for sealingly enclosing the area surrounded by the interior periphery of the base tube. This floor structure includes a plurality of individual inflatable tubular members 50 which provide a cushion of air between the interior of the floor structure 28 and the ground or surface supporting the environmental module of the present invention. The floor structure may consist of a plurality of tubes arranged in concentric circles, a single spiral tube, a plurality of straight tubes of differing lengths or a plurality of adjacent compartments in each case covering the entire area within the base tube 10. All of the tubes 50 are preferably interconnected by suitable air channels so that only a single valve is required to inflate the entire floor support structure. Although the tubes 50 are shown as formed integrally with the floor structure 48, they may also be in the form of a separate air mattress placed under a fluid tight floor panel comprised of a single layer of plastic secured to the tube 10.

The floor structure 48 is securely bonded around its entire periphery to a lower portion of the base tube 10 thereby forming a water-tight fluid pool surrounded by the base tube 10. This pool is preferably filled with a high density liquid such as water having a high concentration of a suitable salt, such as epsom salts ($MgSO_4$) or NaCl dissolved therein, or containing a colloidal suspension of certain insoluble minerals (eg. $x SiO_2 \cdot Al_2O_3$). The fluid is selected to be sufficiently dense to support a floating person 54. The person floating in the pool of liquid 52 floats so that the fluid covers the ears, but the face including nose and mouth project out of the water to enable breathing with no inconvenience.

The air and fluid temperatures within the environmental module are controlled by the equipment contained in the utility module 42, illustrated in block diagram form in FIG. 3. The air circulating system includes an air intake 56 coupled to an air filter 58. Air passing through the filter 58 is directed to a heater 60 which raises the air to a comfortable temperature determined by a thermostat 62. A circulation fan 64 provides the motive power for air circulation. The circulation fan draws air in through the air intake and forces it to pass through the filter 58 and the heater 60, where it is raised to a suitable temperature. The appropriately filtered and heated air is then forced by the circulation fan through the airhose 44 and into the opening 26 at the top of the environmental module. Stale air in the environmental module is subsequently forced out through the door opening 26, which is not completely sealed by the inflatable door panel 28. Alternatively, small exhaust ports may be positioned around the periphery of the environmental module on the side walls thereof near the base tube 10.

The water circulating and conditioning system is similar to the air circulating system. Initially, the above-described pool within the environmental housing is filled with a suitable fluid, such as a heavy salt solution, as mentioned previously. This fluid 52 is then continuously withdrawn from the pool through an outlet hose 66 coupled to a water outlet aperture 68 preferably positioned at the center of the floor structure 48. The fluid passing through the outlet hose 66 is drawn through a fluid filter 70 where impurities are removed, and is subsequently passed through a fluid heater 72, also controlled by the thermostat 62. The fluid temperature is elevated by the heater to a point approximately 5° F below body temperature to enhance the atmosphere of relaxation within the environmental housing. An optional density monitor 74 may also be provided to check the salinity or density of the fluid emerging from the heater 72. The density monitor is not essential to the system of the present invention, but it can be added to insure that the density or salinity of the fluid 52 is maintained within a suitable range. A circulation pump 76 is used to provide the motive force for circulating the fluid 52. The output of the circulation pump is coupled through a fluid input line 78, which is branched into a plurality of individual fluid inputs 80 coupled to suitable apertures located around the periphery of the floor structure 48. Although only two such fluid inputs are shown, it will be understood by those skilled in the art that the fluid inputs can be positioned around the entire periphery of the floor structure 48 in order to insure uniform circulation within the pool of fluid 52. It will be understood, of course, that continuous circulation is maintained between the multiple fluid inputs and the centrally located outlet 68.

It will be understood by those skilled in the art that all of the components included in the utility module 42 are strictly conventional commercially available components, and do not individually comprise any aspect of the present invention. Furthermore, many different types of fans, filters, pumps heaters and thermostats are suitable for use with the present invention, and thus those skilled in the art will be aware that commercially available units can be conveniently selected depending upon the size and volume of the environmental units, so that sufficient air and water conditioning and circulating capacity is provided. It will also be understood by those skilled in the art that the various components illustrated in FIG. 3 may be packaged in a suitable attractive housing of the shape illustrated in FIG. 1, and that the various illustrated hoses may be placed together in a compact assembly as shown in FIG. 1. However, the precise packaging and hose arrangement is not essential to the operation of the apparatus of the present invention, and many alternative packaging and physical arrangements are possible. However, it is important to select equipment that operates at relatively low noise levels and to provide sufficient hose lengths so that the utility module 48 does not generate high sound levels which penetrate the environmental housing. The utility module can be incorporated into the isolation module itself, provided equipment producing very low sound levels is used in the utility module.

Figure 4:
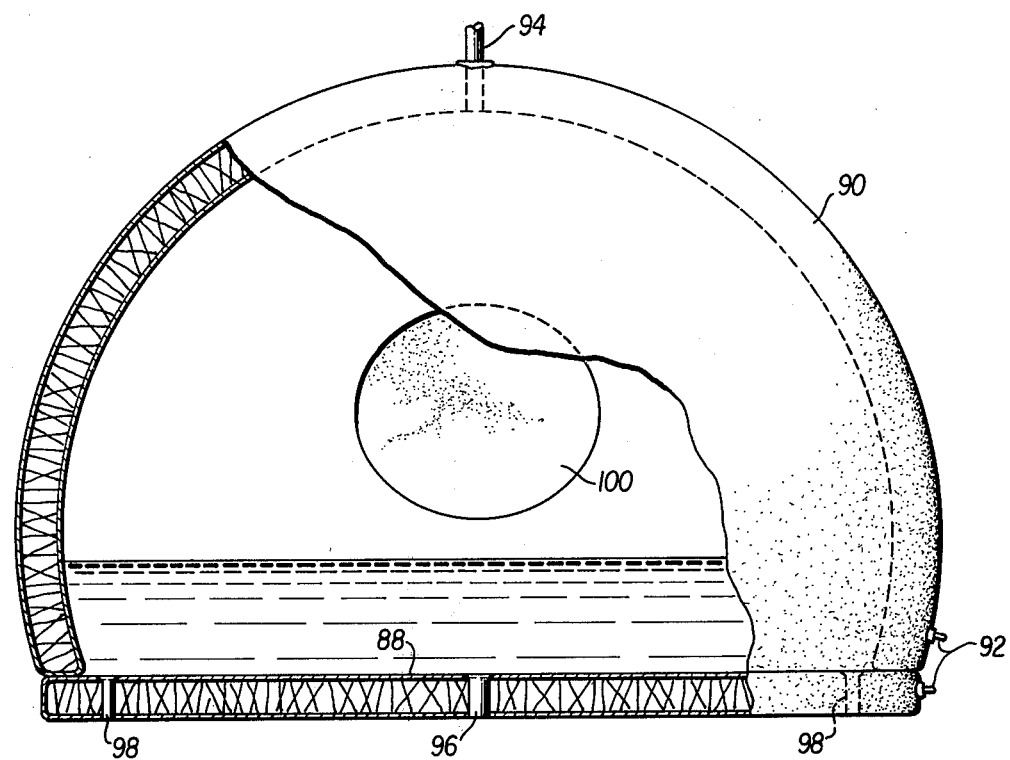
FIG. 4 is an illustration of a second embodiment of the present invention.
Figure 5:
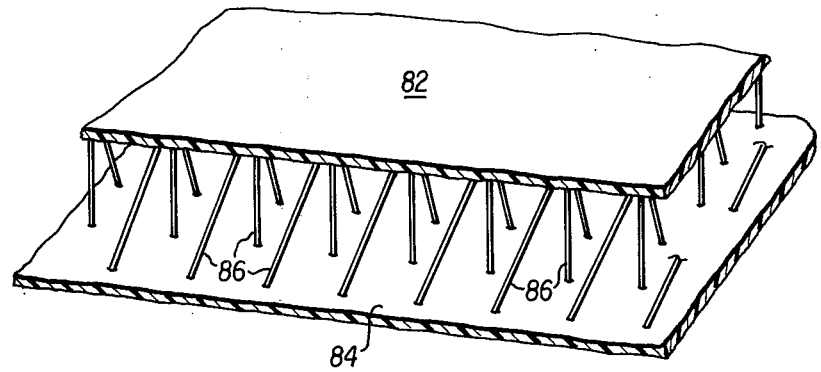
FIG. 5 is a detailed illustration of a portion of the wall structure of the embodiment illustrated in FIG. 4 showing the interconnecting fiber structure thereof.

Attention is now directed to FIG. 4 wherein a second embodiment of the environmental module of the present invention is illustrated. The second embodiment of the present invention includes a unique type of non-cellular wall structure illustrated in detail in FIG. 5. As shown in FIG. 5, the non-cellular wall structure includes a first plastic sheet 82 and a second plastic sheet 84 joined by a large number of flexible stretch-resisting fibers 86. The fibers 86, which may be in the nature of plastic, fiberglass, natural fibers or paper are bonded to the separate sheets of plastic by conventional techniques or may be extruded with the sheets. The fibers 86 limit the maximum separation between the plastic sheets 82 and 84, although they permit the space between the plastic sheets to be reduced to a minimum so that the sheets may be folded, or rolled into a very compact package.

An environmental module using the non-cellular wall structure of FIG. 5 is shown in FIG. 4. This structure preferably includes a single floor panel 88 and an arcuate enclosure panel 90 which may be either semi-circular or cylindrical in configuration when inflated. The enclosure panel 90 is bonded by suitable conventional means to the floor panel 88 to provide a fluid tight seal.

The valves 92 are provided for separately inflating the floor panel and the enclosure panel. These values may be substantially identical to the valves 12 illustrated in conjunction with the previous embodiment of the present invention and may be inflated in the same manner as described above. An air input aperture 94 is provided at the top of the enclosure panel 90 and a suitable fluid outlet opening 96 as well as fluid inlet openings 98 are provided in the floor panel 88. The air and fluid circulating and conditioning system previously described can thus be coupled to the structure illustrated in FIG. 5.

Fluid 52 is poured directly into the base of the environmental structure illustrated in FIG. 5 through a doorway or opening 100, to be supported by the floor panel 88 and to be contained by lower portions of the enclosure panel 90. Thus, the structure illustrated in FIG. 4 is a greatly simplified structure to produce, relative to the previously described embodiment of the invention. It can also easily be constructed in other shapes and configurations although the rounded configurations shown eliminates the need for support poles in view of its generally high level of structural stability when inflated.

In use, the environmental modules disclosed in the present application are first assembled. In the case of the first embodiment of the invention, the support poles are intially inserted into the appropriate pockets and holders on the inflatable structure. The structure is then inflated by appropriate application of air or another suitable gas to the various input valves. The utility module 42, which may be either electrically powered or otherwise powered, depending upon the circumstances of use, is then coupled to the environmental module by coupling the air hose 44 to the air input aperture at the top of the environmental module and by coupling the water input and output hoses to the appropriate inlet and outlet openings in the floor of the structure. A water supply is subsequently poured into the water containing portion of the structure and a quantity of salt is added to the water to increase its density to facilitate flotation. The utility module is then switched on to raise the water and air temperature within the environmental module to the desired levels for maximum comfort and relaxation. It is noted that although only heaters have been described previously, air conditioning and water cooling units can also be provided in the utility module for circumstances in which the external ambient temperature is very high.

Once the module and all of its control systems are operating in their stable states, one or more individuals desiring to isolate themselves from external stimuli enter the environmental module through the door opening, preferably unclothed, and recline in the heated liquid pool. The high density of the liquid permits easy flotation so that the individuals using the environmental module float in the liquid pool 52 substantially as shown in FIG. 3. The water level covers the ears of the individuals, thereby greatly attenuating the level of any sound reaching the individuals. The inflated walls surrounding the interior of the environmental module also greatly reduce the transmission of sound waves into the interior of the module, impede loss of heat, and further attenuate the admission of any intense light, so that the interior of the environmental module becomes a very warm, silent environment in which only a very subdued light is permitted through the walls, which may be slightly translucent, although they may also be totally opaque. The cushion of air beneath the fluid pool substantially prevents the transmission of any ground tremors or accoustic stimuli, transmitted through the ground from reaching the person or persons within the pool. Accordingly, an atmosphere of great comfort and isolation exists within the environmental module to permit profound relaxation without the possibility of interruption for the person or persons within the module. Naturally, it will be apparent by those skilled in the art that the module can be used for purposes other than the profound relaxation described above. It can be used for psychological experimentation, as well as medical treatment, entertainment and numerous other conventional uses.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A portable isolation module for reducing ordinary levels of stimulation comprising:
   an inflatable enclosure of sufficient size to accommodate at least one adult;
   inflatable containing means at the base of said inflatable enclosure containing a pool of a high density liquid of sufficient size for supporting at least one adult in a state of floatation;
   said inflatable containing means including an inflatable bottom portion supporting said liquid on a cushion of contained gas for minimizing the transmission of external stimuli of an accoustic nature into said liquid;
   air supply means coupled to said inflatable enclosure for supplying fresh air to the interior of said enclosure; and
   temperature control means coupled to said inflatable containing means for maintaining the temperature of said high density liquid near normal body temperature.

2. An apparatus as in claim 1, wherein:
   said inflatable enclosure includes a structure including a pair of plastic sheets interconnected by a network of stretch-resisting fibers.

3. An apparatus as in claim 1, wherein:
   said inflatable enclosure includes an inflatable door panel of a size sufficient to permit a human being to enter said enclosure.

4. An apparatus as in claim 1, further comprising:
   an external skeletal frame structure coupled to said inflatable enclosure for increasing the structural strength thereof.

5. An apparatus as in claim 1, wherein:
   said inflatable containing means includes an inflatable tube, the inner surface of which provides a fluid containing boundary.

6. An apparatus as in claim 1, further comprising:
   a water-tight floor panel in said inflatable containing means; and,
   a removable inflatable mattress means for supporting said floor panel to minimize the transmission of accoustic energy to said high density fluid in the interior of said isolation module.

7. An apparatus as in claim 1, wherein:
   said inflatable enclosure includes a plurality of interconnected inflatable panels.

8. An apparatus as in claim 7, further comprising:
   a zipper detachably joining two groups of said inflatable panels.

9. An apparatus as in claim 1, further comprising:
   an inflatable floor structure secured to said inflatable containing means in a fluid tight manner, said floor structure acting to minimize the transmission of accoustic energy into said high density fluid in the interior of said isolation module.

10. An apparatus as in claim 9, wherein:
    said inflatable containing means is filled with a colloidal suspension of selected insoluble minerals.

11. An apparatus as in claim 9, wherein:

said inflatable containing means is filled with a fluid including a solution of a salt and water.

12. An apparatus as in claim 11, wherein:
said salt is MgSO$_4$.

13. An apparatus as in claim 1, wherein:
said air supply means further includes a thermostatically controlled heater; and,
an air filter.

14. An apparatus as in claim 13, wherein:
said air supply means includes a circulating fan.

15. An apparatus as in claim 1, wherein:
temperature control means includes a thermostatically controlled fluid heater; and,
a fluid heater.

16. An apparatus as in claim 15, wherein:
said temperature control means further includes a circulation pump.

* * * * *